United States Patent
Wan et al.

(10) Patent No.: US 9,206,414 B2
(45) Date of Patent: Dec. 8, 2015

(54) ANISOTROPIC NANOCOMPOSITE HYDROGEL

(75) Inventors: Wan-Kei Wan, London (CA); Leonardo Millon, London (CA)

(73) Assignee: AXCELON BIOPOLYMERS CORPORATION, London, ON (CA)

(*) Notice: Subject to any disclaimer, the term of this patent is extended or adjusted under 35 U.S.C. 154(b) by 1016 days.

(21) Appl. No.: 12/379,384

(22) Filed: Feb. 19, 2009

(65) Prior Publication Data
US 2009/0252800 A1 Oct. 8, 2009

Related U.S. Application Data

(63) Continuation-in-part of application No. 12/216,809, filed on Jul. 10, 2008, which is a continuation of application No. 10/639,683, filed on Aug. 13, 2003, now abandoned.

(51) Int. Cl.
| | |
|---|---|
| *A61K 9/14* | (2006.01) |
| *C12N 11/12* | (2006.01) |
| *C08L 29/04* | (2006.01) |
| *C12N 11/04* | (2006.01) |
| *C12P 19/04* | (2006.01) |
| *C08L 1/02* | (2006.01) |

(52) U.S. Cl.
CPC .............. *C12N 11/12* (2013.01); *C08L 29/04* (2013.01); *C12N 11/04* (2013.01); *C12P 19/04* (2013.01); *C08L 1/02* (2013.01)

(58) Field of Classification Search
CPC ........... C12P 19/04; C08L 29/04; C08L 1/02; A61K 31/10; A61K 27/48
See application file for complete search history.

(56) References Cited

U.S. PATENT DOCUMENTS

| | | | |
|---|---|---|---|
| 4,323,492 | A | 4/1982 | Zimmermann et al. |
| 4,469,837 | A | 9/1984 | Cattaneo |
| 4,524,064 | A | 6/1985 | Nambu |
| 4,575,551 | A | 3/1986 | Fujiyama et al. |
| 4,588,400 | A | 5/1986 | Ring et al. |
| 4,656,216 | A | 4/1987 | Muller et al. |

(Continued)

FOREIGN PATENT DOCUMENTS

| | | |
|---|---|---|
| EP | 0860471 | 11/2002 |
| JP | 07216244 | 8/1995 |

(Continued)

OTHER PUBLICATIONS

Millon et al., (J Biomed Mater Res B Appl Biomater. Nov. 2006;79(2):305-11).*

(Continued)

*Primary Examiner* — Cherie M Stanfield
(74) *Attorney, Agent, or Firm* — Lynn C. Schumacher; Stephen W. Leonard; Hill & Schumacher

(57) ABSTRACT

Anisotropic nanocomposite hydrogel materials are created using a process in which a hydrogel-forming material is crosslinked in the presence of nanoscale cellulose and subsequently thermally cycled under an applied tensile strain. Such materials are capable of exhibiting high mechanical and viscoelastic anisotropy, increased stiffness when subjected to large strain, and are suitable for a broad range of soft tissue replacement applications. In addition controlled release of bioactive agents properties can be designed into medical devices fabricated from such nanocomposite materials.

28 Claims, 11 Drawing Sheets

(56) References Cited

U.S. PATENT DOCUMENTS

| | | | |
|---|---|---|---|
| 4,663,358 A | | 5/1987 | Hyon et al. |
| 4,742,164 A | * | 5/1988 | Iguchi et al. .................. 536/56 |
| 4,851,168 A | | 7/1989 | Graiver et al. |
| 4,865,552 A | | 9/1989 | Maloney et al. |
| 5,256,418 A | | 10/1993 | Kemp et al. |
| 5,336,551 A | | 8/1994 | Graiver et al. |
| 5,374,539 A | | 12/1994 | Nimni et al. |
| 5,558,861 A | * | 9/1996 | Yamanaka et al. ........... 424/93.7 |
| 5,716,370 A | | 2/1998 | Williamson, IV et al. |
| 5,846,213 A | * | 12/1998 | Wan ................................ 602/49 |
| 5,944,754 A | | 8/1999 | Vacanti |
| 5,958,420 A | | 9/1999 | Jenson |
| 5,989,244 A | | 11/1999 | Gregory et al. |
| 5,990,379 A | | 11/1999 | Gregory |
| 6,117,979 A | | 9/2000 | Hendriks et al. |
| 6,156,531 A | | 12/2000 | Pathak et al. |
| 6,166,184 A | | 12/2000 | Hendriks et al. |
| 6,231,605 B1 | | 5/2001 | Ku |
| 6,372,228 B1 | | 4/2002 | Gregory |
| 6,458,156 B1 | | 10/2002 | Wan et al. |
| 6,855,743 B1 | | 2/2005 | Gvozdic |
| 8,551,502 B2 | * | 10/2013 | Wan et al. ..................... 424/400 |
| 2001/0044138 A1 | | 11/2001 | Watanabe et al. |
| 2002/0128234 A1 | * | 9/2002 | Hubbell et al. ............... 514/100 |
| 2003/0118560 A1 | | 6/2003 | Kelly et al. |
| 2004/0096509 A1 | | 5/2004 | Hutchens et al. |
| 2005/0106255 A1 | | 5/2005 | Ku |
| 2009/0214623 A1 | | 8/2009 | Wan et al. |

FOREIGN PATENT DOCUMENTS

| | | |
|---|---|---|
| JP | 2004085844 | 3/2004 |
| WO | 96/11721 | 4/1996 |
| WO | 01/30145 | 5/2001 |
| WO | 2004046229 | 6/2004 |
| WO | 2006102756 | 10/2006 |

OTHER PUBLICATIONS

Wan et al., "Optimizing the Tensile Properties of Polyvinyl Alcohol Hydrogel for the Construction of a Bioprosthetic Heart Valve Stent", Journal of Biomedical Materials Research (Applied Biomaterials) 2002, 63, pp. 854-861.

Hirai, T. et al. Effect of Chemical Cross-linking under Elongation on Shape Restoring of Poly(vinyl alcohol) Hydrogel. Journal of Applied Polymer Science. 46. 8. pp. 1449-1451. 1992.

Stauffer, S.R. et al. Poly(vinyl alcohol) hydrogels prepared by freezing-thawing cyclic processing. Polymer. 33 (18). pp. 3932-3936. 1992.

Hassan, C. M. et al. Structure and Applications of Poly(vinyl alcohol) Hydrogels Produced by Conventional Crosslinking or by Freezing/Thawing Methods. Advances in Polymer Science. vol. 153. pp. 37-65. 2000.

Chen et al. Boundary layer infusion of heparin prevents thrombosis and reduces neointirnal hyperplasia in venous polytetrafluoroethylene grafts without systemic anticoagulation. J. Vascular Surgery. vol. 22. pp. 237-247. 1995.

Makoto Suzuki. An Artificial Muscle by PVA Hydrogel can Generate High Power Close to Living Skeletal Muscle's. Ieee Engineering in Medicine & Biology Society 11th Annual International Conference. CH2770-618910000-0916. C IEEE. pp. 0913-0917. 1989.

Tatsuo Kaneko et al. Mechanically Drawn Hydrogels Uniaxially Orient Hhdroxyapatite Crystals and Cell Extension. American Chemical Society. Chem. mater. vol. 16. No. 26. pp. 5596-5601. 2004.

Millon et al. Anisotropic Polyvinyl Alcohol Hydrogel for Cardiovascular Applications. Journal of Biomedical Materials Research (2005). Wiley Inter Science (2006). pp. 305-311.

* cited by examiner

ANISOTROPIC NANOCOMPOSITE HYDROGEL

RELATED U.S. APPLICATION DATA

This application is a continuation-in-part of application Ser. No. 12/216,809, filed, Jul. 10, 2008, currently pending, which is a continuation of application Ser. No. 10/639,683, filed Aug. 13, 2003, abandoned, both of which are incorporated herein by reference in their entirety.

FIELD OF THE INVENTION

This invention relates to nanocomposite anisotropic hydrogels, including methods of their preparation and uses thereof, and more particularly this invention relates to nanocomposite anisotropic hydrogels that are crosslinked in the presence of bacterial cellulose.

BACKGROUND OF THE INVENTION

Heart disease and stroke, which are the principal components of cardiovascular disease, remain the leading cause of death in the western world. One of the most common treatments for coronary artery disease is coronary bypass graft surgery (CABG), where a suitable length of the patient's saphenous vein or the internal thoracic or mammary arteries are used to supply blood to the heart tissue. The number of CABG procedures in the US was more than 600,000 (1.2 million worldwide) in the year 2000, but these tissue grafts tend to deteriorate due to further advancement of the patient's coronary artery disease and disruption of the normal vascularity.[1-3] On the other hand, total peripheral artery bypass grafting is performed to relieve the symptoms of vascular deficiencies, where a common problem involves the supply of autologous bypasses. The lack of nondiseased saphenous veins as arterio-venous access fistulae for haemodialysis is a major cause of morbidity for patients with renal failure.[4, 5]

From the composition point of view, it is important to note that cardiovascular tissues are composite materials with elastin and collagen as the main load bearing components. The directional manner in which collagen fibers are arranged within the tissue creates the anisotropic behavior, with higher tensile strength in the circumferential than in the axial direction.[6-9]. Accordingly, the mechanical properties of soft tissues, including aortic tissue, are anisotropic, with a higher stiffness in the circumferential than in the axial direction.

For a biomaterial to be used as tissue replacement, it is important to ensure a good match of the mechanical properties of the implanted device and the surrounding tissues [10]. Elastic polymers have been investigated to create compliant grafts since the mismatch of the native aorta and the synthetic grafts, such as Dacron and ePTFE, may contribute to intimal hyperplasia (IH) and ultimate failure. A successful replacement has been reported as having adequate strength, kink resistance, and must allow sutures to hold under circumferential and axial tension, as well as circumferential and axial compliance. Difference in compliance results in haemodynamic changes and increased shear stresses that may induce the release of growth factors that stimulate IH.[10-12].

Even though there are several FDA approved materials for replacement aorta, such as Dacron or e-PTFE, these materials do not posses the same tensile properties as the tissue they are replacing, which results in hemodynamic problems and mismatch of mechanical properties and other problems at the implant/tissue junction. Therefore, it would be very advantageous to be able to produce a material that provides a suitable match with the mechanical and viscoelastic properties of biological tissues. Two promising material systems for meeting this need are anisotropic hyrdrogels and nanocomposite hydrogels, as described below.

Hydrogels

Hydrogels have been shown to be promising candidates for a wide range of biocompatible tissue replacement materials. Hydrogels are hydrophilic polymer networks produced from reactions of one or more monomers or by association bonds between chains that can absorb from at least 20% to up to thousands of times their dry weight in water [13, 14]. Hydrogels may be chemically stable or they may disintegrate and dissolve with time. They are called either physical (reversible) or chemical (permanent) hydrogels. Physical hydrogels have networks held together by molecular entanglements and/or secondary forces such as hydrogen bonding, van der Waals interactions, ionic or hydrophobic forces. Physical hydrogels are not homogeneous due to regions of high crosslinking density and low water swelling, called clusters, dispersed within low crosslinking density and high water swelling, or hydrophobic or ionic domains that create inhomogeneities. Chemical hydrogels are covalently crosslinked networks, but they may also be generated by crosslinking of water-soluble polymers, or by converting hydrophobic polymers to hydrophilic polymers. Chemical hydrogels are also not homogeneous due to clusters of molecular entanglements. Chain loops and free chain ends also produce network defects in both physical and chemical hydrogels, and they do not contribute to the permanent network elasticity [13, 15].

The main areas in which hydrogels are used as biomaterials is in contact lenses, synthetic wound coverings, drug delivery systems, organ and tissue replacements, and permselective membranes [13, 16, 15, 17-24].

An important characteristic of hydrogels is their swelling behaviour in water, since after preparation they have to be in contact with water to yield the final solvated network structure. Highly swollen hydrogels are those of polyvinyl alcohol (PVA), polyethylene glycol, and poly-N-vinyl 2-pyrrolidone, among others. PVA is a hydrophilic polymer with various characteristics desired for biomedical applications, such as high degree of swelling, uncomplicated chemical structure, rubbery/elastic nature, and non-toxic. PVA can be converted into a solid hydrogel by crosslinking.

Crosslinking can be accomplished by using several methods. For biomedical applications, physical crosslinking has the advantages of not leaving residual amounts of the toxic crosslinking agent, and higher mechanical strength than the PVA gels crosslinked by either chemical or irradiative techniques.

The mechanical properties of the PVA hydrogels are similar to that of soft tissue, including elasticity and strength, and can be controlled by changing the number of thermal cycles, PVA concentration, thawing rate of the thermal cycling process, and freezing holding time among other parameters [19, 25, 26]. A PVA based bioprosthetic heart valve stent has been fabricated. However, the mechanical strength and stiffness of these PVA materials were weak and did not fully match the mechanical properties displayed by the cardiovascular tissues such as arteries and heart valves.

PVA has a relatively simple chemical formula with a pendant hydroxyl group and a crystalline nature, which allows it to form a solid hydrogel by the crosslinking of the PVA polymer chains. Vinyl alcohol (monomer) does not exist in a stable form and rearranges to its tautomer, acetaldehyde. PVA is produced by free radical polymerization of vinyl acetate to polyvinyl acetate (PVAc), and subsequent hydrolysis of PVAc gives PVA [25].

PVA can be crosslinked using several methods, such as the use of crosslinking chemical agents, using an electron beam or γ-irradiation, or the physical crosslinking due to crystallite formation. For biomedical applications, physical crosslinking has the advantages of not leaving residual amounts of the toxic crosslinking agent, and higher mechanical strength than the PVA gels crosslinked by either chemical or irradiative techniques [27, 28]. In chemical cross-linking, the chemical agents that react with the hydroxyl groups are glutaraldehyde, ethylaldehyde, terephthalaldehyde, formaldehyde, hydrochloric, boric or maleic acid, among others [19, 29].

Physical crosslinking forms a hydrogel with a network of semi-crystallites of hydrogen bonds of polymer filled with solvent [30]. It has been shown that the mechanical properties of the hydrogels, including elasticity and strength, can be altered by changing the PVA concentration, the number of freeze/thaw cycles, the process thawing rate, the freezing holding time, and the freezing temperature [19, 29, 30]. Increasing the PVA concentration results in hydrogels with higher crystallinity and added stability upon swelling, which increases its tensile strength and tear resistance. The lower the initial concentration of PVA, the fewer the polymer chains in solution, and there may be less number of crystalline regions created in the cycled PVA. Increasing the number of freeze/thaw cycles increases the strength and stiffness of the hydrogel by reinforcing existing crystals within the structure [19, 25, 26]. Decreasing the thawing rate of frozen PVA solutions increases the tensile strength because the solutions are kept for longer periods at temperatures below 0° C., allowing for increasing movements of polymer chains which result in further entanglements and increased crystallite size and numbers.

The freezing holding time also has a drastic effect, with samples frozen up to 10 days giving the most mechanically strong PVA hydrogels [19, 26, 28, 29]. The freezing temperature has an interesting effect. The freezing temperature controls the phase equilibria and dynamics, where the lower the temperature of the system the lower the amount of unfrozen solvent in the liquid regions. Therefore, the lower the temperature the less opportunity for chain mobility in the polymer rich regions, giving less chances of crystallite growth and formation. This explains why keeping the frozen PVA solutions at −10° C. produces somewhat more rigid hydrogels than those kept for the same period of time at −20 or −30° C. The freezing rate was shown not to have drastic effects on the properties of the hydrogel [19, 26, 30]. PVA hydrogels not only have tensile strength and elongation, but also flexibility and elasticity. Research has proven its ability to recover to its original shape after being deformed to strains of 50%, showing excellent persistence and repeatability of the recovery [30].

Physical crosslinking allows the PVA hydrogels to retain their original shape and be extended up to six times their size. This behaviour shows its rubbery and elastic nature and the high mechanical strength [24, 31]. There are various theories proposed in the literature to explain why thermal cycling increases the elastic modulus of PVA. The most accepted theory describes the physical cross-linking process as an entropic reordering phenomena. Water is likely to bind to the polymer by hydrogen bonding. When the solution freezes, ice crystals force the polymer chains close to each other forming high local polymer concentration regions or nuclei. When the material thaws, these nuclei act as crosslinking sites for polymers molecules, which realign and form hydrogen bonds to form crystallites and polymer chain entanglements. The crystalline regions are formed within the polymer rich regions, with further cycling increasing both the size and number of the crystalline regions by repeating the process [19, 32, 27]. On a molecular level, the crystallites of PVA can be described as layered structure, with a double layer of molecules held together by hydroxyl bonds, while weaker van der Waals forces operate between the double layers. This folded chain structure leads to ordered regions (crystallites) within an unordered, amorphous polymer matrix [25]. The mechanical properties of PVA are very unique compared to other polymers. The stress-strain curves for the polymeric materials are initially linear and then curve towards the strain axis. On the other hand, the PVA curve displays an exponential stress-strain curve similar to the characteristics of soft biological tissues, with the curve shifting towards the stress axis.

PVA materials have been reported to be ideal candidates as biomaterials, due to their high degree of swelling, uncomplicated chemical structure, rubbery/elastic nature, non-toxic, non-carcinogenic, and bioadhesive characteristics. Some of the biomedical applications include tissue reconstruction and replacements, cell entrapment and drug delivery, soft contact lens material, wound covering bandage for burn victims, quality control phantom for MR, among other medical applications [32, 25].

Anisotropic Hydrogels

Most research PVA hydrogels has focused on materials exhibiting the normal characteristic of isotropic mechanical behaviour, that is, the mechanical properties of the material are the same regardless of orientation. This is expected due to the random distribution of the polymer chains.

Most tissues, however, including cardiovascular tissues, are composite viscoelastic biomaterials displaying mechanical properties with varying degrees of orientation effects. This orientation effect is due to the organization of the structural protein components such as collagen and elastin within the tissue. This organization gives rise to the unique exponential stress-strain relationship exhibited by soft tissues.

Recently, an anisotropic PVA hydrogel was reported [33] that was able to closely match the stress-strain behaviour of porcine aorta. In this study, it was shown that an anisotropic PVA hydrogel can be produced that displays the exponential response of cardiovascular tissue and also displays the anisotropic behavior of porcine aorta up to 65% strain.

Nanocomposite Hydrogels

A second material system for obtaining improved viscoelastic properties of synthetic and biocompatible replacement tissue materials is that of nanocomposite hydrogels.

Bacterial cellulose has many characteristics that make it valuable for biomedical applications, including its polyfunctionality, hydrophilicity, and biocompatibility [34]. Cellulose is a linear polymer made of glucose molecules linked by β(14) glycosidic linkages. Its chemical formula is $(C_6H_{10}O_5)_n$. There are four principle sources of cellulose. The majority of cellulose is isolated from plants. A second source is the biosynthesis of cellulose by different microorganisms, including bacteria (*acetobacter*, aerobacter, pseudomonas), algae, and fungi among others. The other two less common sources include the enzymatic in vitro synthesis starting from cellobiosyl fluoride, and the chemosynthesis from glucose by ring-opening polymerization of benzylated and pivaloylated derivatives [35, 36]. Cellulose is not uniformly crystalline, but ordered regions are extensively distributed throughout the material, and these regions are called crystallites. The long cellulose chains lie side by side held together by hydrogen bonds between the hydroxyl groups. These chains are twisted into structures called microfibrils, which are twisted into fibers [34, 35].

Bacterial cellulose is produced by strains of the bacterium *Acetobacter xylinum*, which is typically found on decaying fruits, vegetables, vinegar, fruit juices, and alcoholic beverages. It is a Gram-negative, rod shaped and strictly aerobic bacterium. Bacterial cellulose produced has very high purity and contains no lignin, hemicelluloses, pectin, and waxes as plant cellulose does. Therefore, production of bacterial cellulose has the advantage of not requiring the harsh chemical treatment needed for plant cellulose production. This chemical treatment also has the disadvantage of altering the natural structural characteristics of cellulose [34, 35, 36]. Bacterial cellulose differs from plant cellulose with respect to its high crystallinity, ultra-fine network structure, high water absorption capacity, high mechanical strength in the wet state, and availability in an initial wet state [36].

Bacterial cellulose pellicles are formed in static culture. The pellicle has an ultra-fine network structure of ribbons 500 nm wide and 10 nm thick. The ribbons consisted of smaller microfibrils with a width of around 3 nm and a fiber diameter of less than 130 nm compared to the over 14 mm found in birch [35, 36]. Bacterial cellulose including the pellicle possesses a high water retention capacity. Water retention values can reach up to 1000%, which are significantly higher than that for plant cellulose. The water retention is drastically decreased after air-drying the bacterial cellulose and reswelling in water, with values comparable to those of plant cellulose [35, 36].

Bacterial cellulose can also be prepared in shake culture in flasks and in agitated culture in a bioreactor. These approaches are more efficient methods for bacterial cellulose production and are preferred for large scale production of bacterial cellulose.

Bacterial cellulose, being a hydrophilic, highly water swollen and biocompatible natural polymer which is ideally suited to be the reinforcing fibers in the preparation of a nanocomposite material for soft tissue replacement devices. Such nanocomposite material can be created when it is used in combination with PVA.

Uryu [37] reported the formation of a biodegradable polymeric material that can be decomposed in soil. The bacterial cellulose (with ribbon shaped micro-fibrils) that can be biologically decomposed by microbes was mixed with a biodegradable polymeric material to produce an improved composite with higher tensile strength. The bacterial cellulose was produced in a liquid culture medium using different types of, microbes, including *Acetobacter xylinum*, collected and dried into a powdery state and mixed with the polymer to produce the composite. Various polymers were used, including PVA. The nanocomposites ranged from bacterial cellulose concentrations as low as 1% to 99%. The final composite was dried and used for high-strength cabinets for audio/video apparatus. After the lifetime of the device is reached, the composite material can be buried in the ground for waste disposal and it is eventually decomposed to protect the environment.

U.S. Pat. No. 5,558,861 discloses a hydrogel formed by microbially-produced cellulose that may be complexed with an appropriate auxiliary material (including PVA) for the purposes of reinforcement, change of the specific gravity, immobilization, modification of the affinity, prevention of exudation of the liquid component and the like. This invention teaches a hydrogel that is formed based on the crosslinking of bacterially cellulose, whereby a concentration of PVA can be added for a number of purposes, including reinforcing the crosslinked bacterial cellulose hydrogel.

In contrast to the hydrogel disclosed in U.S. Pat. No. 5,558,861, U.S. patent application Ser. No. 12/216,809 teaches a nanocomposite hydrogel comprising PVA and bacterial cellulose, where the hydrogel is formed by physically crosslinking a PVA solution with a small concentration of bacterial cellulose. This composite hydrogel, in which PVA forms the primary structure of the hydrogel rather than a reinforcing structure, uniquely provides a biocompatible composite hydrogel that exhibits the exponential stress-strain behaviour that is characteristic of many biological tissues.

The nanocomposite hydrogel of U.S. patent application Ser. No. 12/216,809 can be further understood by considering the development of the hydrogel during crosslinking, and the role of the bacterial cellulose in this process. The bacterial cellulose, which forms extensive hydrogen bonds with PVA, is believed to act as a nucleation site for the formation of additional PVA crystallites during crosslinking. Accordingly, the composite hydrogel can be understood to be formed by crosslinking PVA in the presence of bacterial cellulose nanofibers, where the bacterial cellulose promotes additional PVA crystal growth and also contributes to the over strength and compliance properties of the composite [38].

The Need for Additional Stiffness and Anisotropy

For cardiovascular applications, it is important to consider the full strain range that is required in clinical applications. The physiological average strain between diastole and systole for porcine aorta is around 30% strain [33,38,40]. The physiological strain range has also been reported to be between 17 and 49% strain [40, 41]. However, in designing cardiovascular devices, it is necessary to make allowance for higher strain conditions (corresponding to higher systole values) to ensure the material remains elastic at higher strains to ensure durability. Furthermore, a successful replacement must have adequate strength, kink resistance, and must allow sutures to hold under circumferential and axial tension, as well as circumferential and axial compliance [39].

Accordingly, a need remains for a tissue replacement material that can match the highly anisotropic viscoelastic properties of many different types of soft tissues and can also provide improved stiffness beyond typical physiological strain conditions.

SUMMARY OF THE INVENTION

The present invention addresses this need by providing a process for the production of an anisotropic composite hydrogel that exhibits high anisotropy and increased stiffness at high strain. The novel anisotropic composite hydrogel is suitable for soft tissue replacement, the controlled release of bioagents and in the design and fabrication of medical devices.

In one aspect of the invention there is provided a process of producing a nanocomposite hydrogel with an anisotropic stress-strain curve, comprising the steps of preparing a solution containing a solvent, a first concentration of a hydrogel-forming material and a second concentration of cellulose, wherein said cellulose comprises fibers having nanometer scale cross sectional dimensions, crosslinking the hydrogel-forming material to obtain a nanocomposite hydrogel, applying a tensile force to said nanocomposite hydrogel, and thermal cycling said nanocomposite hydrogel over a predetermined temperature range at least once while maintaining the tensile force.

In a particular aspect of the invention, the hydrogel-forming material is polyvinyl alcohol (PVA) and the cellulose is bacterial cellulose, the concentrations of PVA and bacterial cellulose are about 5% to 25% and 0.05% to 1%, respectively, and the nanocomposite hydrogel is formed by physically crosslinking using the low temperature thermal cycling method.

The present invention also provides an anisotropic nanocomposite hydrogel produced according to the aforementioned processes. The anisotropic nanocomposite hydrogel preferably comprises a composite hydrogel formed by physically crosslinking PVA in the presence of bacterial cellulose, where the concentrations of PVA and bacterial cellulose are about 5% to 25% and 0.05% to 1%, respectively, and the nanocomposite hydrogel is formed by physically crosslinking using the low temperature thermal cycling method.

Also included in the scope of the invention is the use of an anisotropic nanocomposite hydrogel produced according to the process of the invention for tissue replacement, tissue reconstruction, bioagent entrapment, bioagent delivery, preparing ultrasound or radiofrequency thermal therapy transmission pads, preparing substitutes for ice bags, as a denture base, in soft contact lens material, wound covering bandages, neurological dressings, dental implants, catheter covering dressing, dialysis membranes, coatings for cardiovascular stents, coatings for cranial stents, and membranes for tissue guided regeneration and phantoms for medical-related uses.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION OF THE INVENTION

Figure 1:
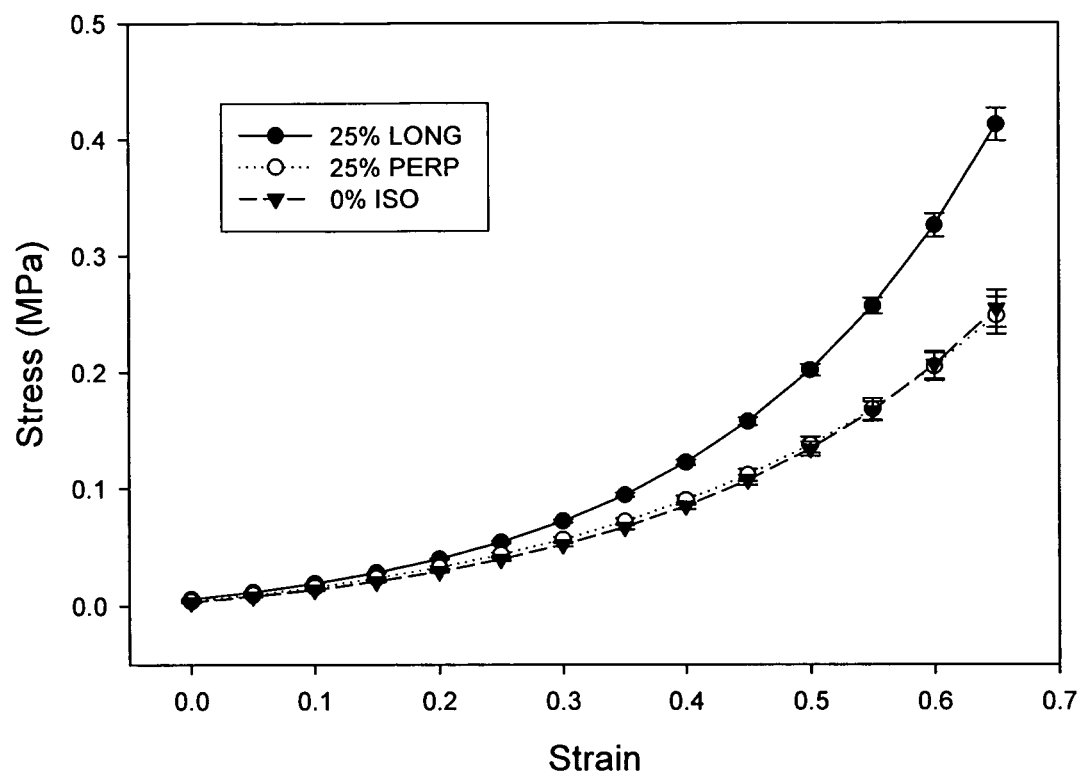
FIG. 1 shows the effect of 25% initial strain on the stress-strain curves of anisotropic 10% PVA with 0.3% bacterial cellulose, following 6 thermal cycles.

The present invention provides a biocompatible anisotropic nanocomposite hydrogel material for soft tissue replacement that provides viscoelastic properties that can be tailored to be highly anisotropic and highly resilient. Unlike prior hydrogel materials, this nanocomposite hydrogel can match the highly anisotropic viscoelastic properties of many different types of soft tissues and can also provide improved stiffness beyond typical physiological strain conditions. The invention is the result of experimentation involving nanocomposite hydrogels comprising PVA and bacterial cellulose, where it was discovered that applying a tensile force while thermal cycling the nanocomposite generated a nanocomposite material with much higher anisotropy and stiffness at large strains than a non-composite material with PVA alone.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention.

As used herein, the terms "about", and "approximately" when used in conjunction with ranges of concentrations, temperatures or other physical or chemical properties or characteristics is meant to cover slight variations that may exist in the upper and lower limits of the ranges of properties/characteristics.

As used herein, the phrase "cellulose of microbial origin" means "microbial cellulose" in addition to other microbes (yeasts, fungi) besides bacteria.

The anisotropic nanocomposite hydrogel of the present invention is produced by crosslinking a nanocomposite hydrogel and subsequently imparting anisotropy to the hydrogel nanocomposite by applying and maintaining a tensile force during one or more thermal cycles. The nanocomposite hydrogel is comprised of a hydrogel-forming material and cellulose, where the cellulose has cross-sectional dimensions on the nanometer scale.

In a preferred embodiment, the hydrogel-forming material is Polyvinyl alcohol (PVA), which is known to produce hydrogels with exponential stress-strain curves that are desirable for soft tissue replacement materials. Alternatively, the hydrogel-forming material can be chosen from the list including polyvinyl alcohol (PVA), poly(vinyl pyrrolidone) (PVP), poly(ethylene glycol) (PEG), poly(hydroxyethyl methacrylate) (PHEMA) and polyacrylamide.

The cellulose is preferably bacterial cellulose, which is known to comprise fibers with typical diameters on the nanometer scale. The bacterial cellulose may be produced in its original as-produced state and not dried but used directly to produce the nanocomposite. The preferred bacterial cellulose is produced using a microbial fermentation process using the bacteria *Acetobactor xylinum* in either a static, shaken or agitated culture as disclosed in U.S. Pat. No. 5,846,213 (which is incorporated herein by reference).

The nanocomposite hydrogel is initially obtained by dissolving the hydrogel-forming material and the nanoscale cellulose in a solvent, followed by crosslinking the hydrogel-forming material to obtain a nanocomposite hydrogel. In a preferred embodiment, the concentration of the hydrogel-forming material may be in the range of about 5% to 25%, and the concentration of nanoscale cellulose may be in the range of about 0.05% to 1%. In embodiments including PVA as the hydrogel-forming material, the PVA solution (suitably with a MW of 146,000 to 186,000, 99+% hydrolyzed) may be prepared by heating, for example at a temperature of about 80° C. to about 100° C., suitably at about 90° C., for an amount of time to achieve the desired solution, for example for about 2 to about 4 hours, suitably about 3 hours.

The solvent used to produce the hydrogel is preferably water, and more preferably distilled water. In embodiments including PVA as the hydrogel-forming material, the solvent may also be chosen from the list of hydroxylic solvents including alcohol, ketone and aldehyde or carboxylic acid, or any other aprotic solvent capable of forming effective hydrogen bonding to dissolve PVA. Examples of dipolar aprotic solvents which may be used include dimtheyl sulfoxide (DMSO), dimethyl formamide (DMF), dimethyl acetamide (DMAc) and N-methyl pyrrolidone (NMP).

If the solvent is not water, the solvent would have to be removed by solvent exchange with water by immersion in water before use. As described above, the nanocomposite material can either be prepared using water as the solvent or solvent systems consisting of combinations of water and other solvents. The final product consists of microbial cellulose, hydrogel and the solvent used. In the case when either water is used in combination with other solvents or when solvent systems not containing water are used in the fabrication process, an additional step of solvent exchange with water will be necessary to replace the non-water solvent before the resulting product can be used for biomedical applications The hydrogel is preferably physically crosslinked, although the hydrogel may also be obtained by chemical crosslinking. In embodiments including PVA as the hydrogel-forming material, the hydrogel nanocomposite is preferably produced by physically crosslinking the solution containing PVA and nanoscale cellulose by the low temperature thermal cycling method.

As described above, anisotropy is imparted to the nanocomposite hydrogel, following crosslinking of the nanocomposite hydrogel, by the application of a tensile force during one or more thermal cycles. In one embodiment, the tensile stress is applied after transferring the crosslinked nanocomposite hydrogel into a vessel capable of applying a tensile force.

The thermal cycling preferably includes a freeze-thaw cycle, whereby the temperature is maintained for a predetermined holding time prior the thawing. In a preferred embodiment, the thermal cycle temperature range lies within the range of approximately +30° C. to −30° C. In another preferred embodiment, the step of thermal cycling the nanocomposite hydrogel involves cooling the nanocomposite hydrogel from a first temperature of about 15° C. to 30° C. to a second temperature of about −15° C. to −30° C., maintaining said second temperature for a holding time, and heating said nanocomposite hydrogel back to a temperature approximately equal to said first temperature. The rate of change of temperature during thermal cycling includes the range of approximately 0.5° C./min to 0.05° C./min, and is preferably about 0.1° C./min. The holding is preferably about 1 hour.

The applied tensile force preferably generates a strain in the nanocomposite hydrogel of up to 100% of the initial length, where the length is measured along the axis of applied force. Preferable, the applied force produces a strain within the range of 60% to 90%, and is chosen to tailor the resulting anisotropic stress-strain curve to the specific application.

The nanocomposite hydrogel can be thermally cycled one or more times while applying the tensile force producing anisotropy. In a preferred embodiment, the nanocomposite hydrogel is thermally cycled 1 to 6 times. In another embodiment, the nanocomposite hydrogel is thermally cycled a predetermined number of times whereby the magnitude of the resulting anisotropy is similar to the anisotropy of a biological tissue or material.

In another embodiment of the invention, the nanocomposite hydrogel is formed into a pre-selected shape for use in medical or therapeutic applications, including planar sheets for wound dressing, dental implants, vascular grafts, synthetic replacement vessels such as aorta (large diameter) and coronary arteries (small diameter), synthetic heart valve leaflets, synthetic cartilage, ligaments and skin catheter covering dressing, dialysis membranes, coatings for cardiovascular stents, coatings for cranial stents, and membranes for tissue guided regeneration.

The amount of anisotropy and ultimate mechanical properties parameters of the anisotropic nanocomposite hydrogel can be controlled by altering several processing parameters. These processing parameters include, but are not limited to, the list including the concentrations of hydrogel-forming material and nanoscale cellulose, the temperature range and rate of thermal cycling, the holding time during thermal cycling, the magnitude of applied tensile force, the number of thermal cycles, and the choice of solvent.

As described above, the anisotropic nanocomposite hydrogel produced according to the process of the present invention provided the unexpected results of significantly higher anisotropy and higher stiffness at large strains when compared to non-composite anisotropic hydrogels. Insight into these novel properties of the nanocomposite hydrogel can be gained by considering the role of bacterial cellulose in the formation of the nanocomposite material.

Bacterial cellulose nanofibers are biocompatible, very hydrophilic, have high strength, and because of the large surface area, are expected to interact strongly by hydrogen bonding with the PVA polymer matrix [34, 36, 38, 42]. As discussed in previous studies for PVA, during the freeze/thaw cycles, ice crystals in the amorphous regions force the polymer chains into regions of high local polymer concentration (polymer mesh), forming crystallites [26, 30, 31, 32]. Several studies reported that after the initial cycle a few percent of the chain segment crystallize into 3-8 nm junctions (primary crystallites) separated by amorphous regions of around 20-30 nm in size within the polymer rich regions. These polymer rich regions are surrounded by polymer poor regions (macropores) with dimensions of >100 nm [4347]. Further cycling augments the level of crystallinity by increasing the size of primary crystallites, as well as forming smaller secondary crystallites in-between, transforming the microstructure to a fibrillar network within larger pores (polymer poor region). Bacterial cellulose is a highly crystalline and hydrophilic nanofiber with high mechanical strength [34, 36, 42]. It is also considered to be biocompatible and has been investigated for applications such as blood-contacting scaffolds [36, 48, 49].

The already-formed bacterial cellulose crystallites during thermal cycling could serve as nucleation sites for further organization of the PVA chains, thus favoring the interaction and formation of PVA crystallites around the bacterial cellulose nanofibers during the initial cycle [38]. When the cycle 1 PVA-bacterial cellulose nanocomposite is stretched, the stress would elongate the PVA polymer mesh as well as the polymer poor macropores [42], along with the bacterial cellulose nanofibers which will tend to orient in the direction of the applied stress. This can be contrasted to the re-orientation of the bacterial cellulose fibrils within cellulose pellicles (sheets) embedded in a polymer matrix, in the direction of an applied stress, as reported in the literature [50, 51]. The degree of orientation of the PVA polymer mesh and bacterial cellulose fibers is expected to be proportional to the amount of initial strain. After the hydrogel is held under stress and further cycled, the increase in volume fraction of crystallinity is due mainly to the growth of the primary crystallites around the bacterial cellulose fibers, as well as the formation randomly oriented secondary crystallites, all within the polymer rich phase [42, 45-47]. Since most of the primary crystallites and bacterial cellulose fibers are oriented along the direction of stretch, this explains why the ratio of longitudinal to perpendicular stress increases as the initial strain is increased (see examples below). On the other hand, increasing the number of thermal cycles at a fixed initial strain increases the volume fraction of crystallites (primary and secondary) in the sample's polymer rich phase, regardless of orientation. This explains why the ratio of longitudinal and the perpendicular stress stays constant as the number of thermal cycles is increased if the initial strain is kept constant (see examples below).

The present invention further relates to a medical material, device or apparatus comprising the anisotropic nanocomposite hydrogel obtained by the following the processes described above.

The anisotropic nanocomposite hydrogel of the present invention is particularly useful in surgical and other medical applications as an artificial material for replacing and reconstructing soft tissues in humans and other animals. Soft tissue that may be replaced or reconstructed using the hydrogel of the present invention include, but are not limited to, vascular vessels, such as aorta (large diameter) and coronary arteries (small diameter), heart valve leaflets, heart valve stent, cartilage, ligaments and skin. Accordingly, the present invention further includes an artificial material for replacing and reconstructing soft tissues comprising the anisotropic hydrogel of the present invention. It is an embodiment of the invention that the anisotropic nanocomposite hydrogel is prepared using a method of the present invention.

The anisotropic nanocomposite hydrogel of the present invention can also comprise a bioactive agent to provide the hydrogel with suitable physiological properties for it to be used as a soft tissue replacement. The bioactive agent can be chosen based upon the particular application planned for the replacement, and the particular physiological properties required of the replacement in the application involved. Many such bioactive agents would be released gradually from the hydrogel after implantation, and thereby delivered in vivo at a controlled, gradual rate. The hydrogel can thus act as a bioactive agent delivery vehicle, for example, a drug delivery vehicle. Other bioactive agents can be incorporated in to the hydrogel in order to support cellular growth and proliferation on the surface of the material. Bioactive agents which can be included in the material include, for example, one or more of cell lines, antibodies, cytokines, thrombins, thrombin inhibitors, proteases, anticoagulants, heparin, growth factors, collagen crosslinking inhibitors, matrix inhibitors, glycosaminoglycans and antimicrobial agents. Heparins are particularly suitable agents for incorporating into vascular grafts, because of their anticoagulant properties, and thus their ability to inhibit thrombosis on the surface of the hydrogel.

In order to embed bioactive agents into the hydrogel of the present invention any of a pre-sterilized powder, aqueous solution or aqueous suspension can be mixed into the starting solution containing the hydrogel-forming material. After the bioactive agent is incorporated into solution, it is processed according to the method described herein. Bioactive agents can also be introduced into the hydrogel by placing the hydrogel into a bath containing an aqueous solution of the agent and allowing the agent to diffuse into the hydrogel. Alternatively, one or more bioactive agents may be incorporated into the anisotropic nanocomposite hydrogel after the final thermal cycle is completed.

The concentration of the one or more bioactive agents in the mixture may be selected for the particular application involved. For heparin incorporation into a vascular graft, concentrations will typically range from 1 unit/ml to 1,000,000 units/ml. Lower concentrations may be employed to inhibit coagulation on the graft surface, and higher concentrations will be used where local infusion of heparin into the blood is desired to inhibit thrombosis downstream of the graft [52].

The anisotropic nanocomposite hydrogel of the present invention can be also be used to support the proliferation of eukaryotic cell cultures. Vascular cells such as endothelial cells, smooth muscle cells, and fibroblasts and other connective tissue cells, can thus be incorporated into the hydrogel. Human aortic endothelial cells and human dermal fibroblasts are also compatible with the hydrogels of the present invention. Hydrogels modified by such cell lines are, in turn, especially well adapted for implantation into the human body, and for use as soft tissue replacement parts in the human body. Indeed, replacement parts modified by such cell lines are better able to adapt and adjust to changing physical and physiological conditions in the body, and thereby to prevent any failure of the hydrogel which might otherwise occur. These cellular lines can be incorporated into the hydrogel for example, after it has been produced, via standard cell culture protocol generally known in the art. It is especially effective to culture human aortic endothelial cells and human dermal fibroblasts using direct topical seeding and incubation in cell culture medium.

Also included within the scope of the present invention is a use of an anisotropic nanocomposite hydrogel of the present invention for tissue replacement, tissue reconstruction, bioagent entrapment, bioagent delivery, preparing ultrasound or radiofrequency thermal therapy transmission pads, preparing substitutes for ice bags, as a denture base, in soft contact lens material, wound covering bandages, neurological dressings (to replace for example Duramater™ during brain surgery) and phantoms for medical-related uses.

The invention is further illustrated by the following non-limiting examples.

EXAMPLES

Example 1

Sample Preparation

PVA (Sigma-Aldrich Canada) with a molecular weight (Mw) of 146,000-186,000, 99+% hydrolyzed, was used in all solution preparations. A suspension of 0.625 wt % bacterial cellulose in distilled water was produced in shake flasks by fermentation using the bacteria *Acetobacter xylinum*, as described by Guhados et al.[42]. PVA was added to the bacterial cellulose suspension with additional distilled water to obtain a mixture of 10 wt % PVA with 0.3 wt % bacterial cellulose.

The PVA-bacterial cellulose solution was transferred into seven aluminum molds and placed in the heated/refrigerated circulator, where they were cycled once between 20° C. and −20° C. to give cycle 1 samples. For a study of the effect of initial strain, one of the samples was used as control while the four other samples were transferred into the four custom design molds where they were initially strained by 25, 50, 75, or 100% of the original length. The four stretched samples and the control were cycled 5 more times to obtain cycle 6.

For a study of the effect of number of thermal cycles, samples were prepared for cycles 2, 4 and 6 at a pre-defined initial strain of 75%. The two extra cycle 1 samples were transferred and stretched at a strain of 75%, with extra samples of non-stretched hydrogel (cycle 1) used as controls in each mold. The molds were then cycled and a mold was removed at the end of cycles 2 and 4.

All samples, including the controls, were cut (25×5 mm2) in either longitudinal or perpendicular direction relative to the applied stress (n=5) for tensile testing.

Example 2

Tensile Testing and Analysis

Testing equipment used in the studies consisted of a servo-hydraulic material testing system (INSTRON 8872) equipped with a 1 Kg load cell. Sample thickness was measured using a Mitutoyo thickness tester, and testing was carried out inside a Plexiglas tank filled with distilled water (at 37° C.). All the specimens were secured onto custom designed tissue grips (10 mm grip-to-grip distance), and tensile tests were performed at a crosshead speed of 40 mm/s to a maximum of 65% strain. Prior to the tensile tests, all specimens were preconditioned with 10 loading and unloading cycles. All data obtained was in the form of load-extension, which was then converted into engineering stress-engineering strain, using the sample thickness and the initial gauge length after preconditioning, as reported previously.

The stress-strain data for PVA-bacterial cellulose nanocomposites is nonlinear and takes on the general shape of curving up towards the stress axis. Therefore, the stress-strain data was fitted by Eq. (1):

$$\sigma = y_0 + Ae^{B\epsilon} + Ce^{D\epsilon} \quad (1)$$

Where σ is stress, ε is strain, and $y_0$, A, B, C, and D are curve fitting parameters. The elastic modulus as a function of strain was calculated as the first derivative with respect to strain of Eq. (1).

After preconditioning and tensile testing, some samples (n=3) were strained to the same 65% strain used for tensile testing and held at constant strain for 1 h, while monitoring the load. The raw data in the form of load-time was converted to relative stress remaining-time, relative to the initial stress at time zero. The time dependent properties of all samples were assessed by stress relaxation test. The stress relaxation data was fitted to Eq. (2):

$$\frac{\sigma(t)}{\sigma_0} = \frac{\sigma_R}{\sigma_0} + Ae^{-Bt} + Ce^{-Dt} \quad (2)$$

where σ(t) is the stress at time t, $\sigma_0$ is the initial stress, R is the final stress (t=3600 s), t is time, and A, B, C, and D are curve fitting parameters.

To facilitate data presentation, the following convention was adopted. Samples cut in the direction of applied stress are denoted as (LONG) for longitudinal, and samples cut perpendicular to the applied stress are denoted (PERP). For the porcine aorta data, the circumferential samples are denoted (CIRC) and the axial samples are denoted (AXIAL). Isotropic (nonstrained) samples are denoted (ISO).

Example 3

Effect of Initial Strain

Figure 2:
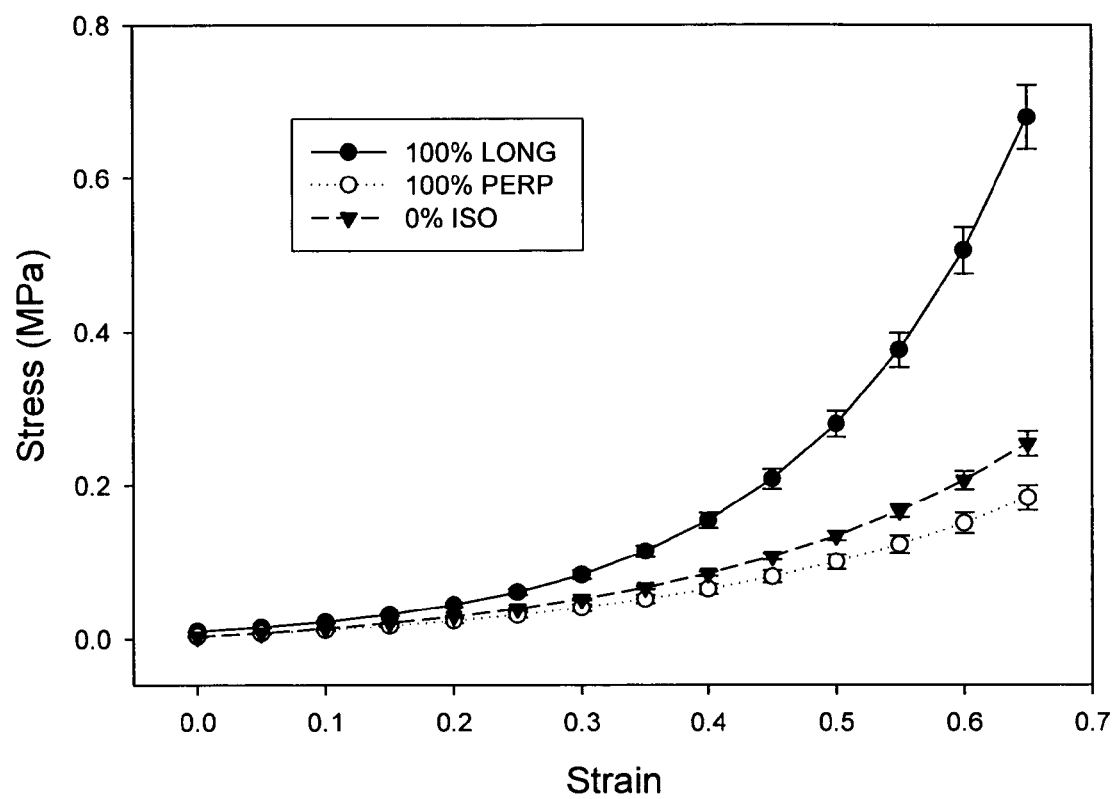
FIG. 2 shows the effect of 100% initial strain on the stress-strain curves of anisotropic 10% PVA with 0.3% bacterial cellulose, following 6 thermal cycles.

FIGS. 1 and 2 show the effect of 25 and 100% initial strains, respectively, on anisotropy relative to the isotropic control. Samples in the longitudinal direction showed higher stiffness than in the perpendicular direction, with the results for isotropic control falling in between or close to the perpendicular direction. Comparing FIGS. 1 and 2, the longitudinal direction displays higher stiffness at the 100% initial strain compared to 25%, as well as a larger difference between the longitudinal and the perpendicular directions. The data in FIG. 1 does not show a statistically significant difference at 65% strain between the perpendicular and isotropic control (p>0.05), but both of them were statistically different from the longitudinal samples (p<0.05). In FIG. 2, a statistically significant difference in stress at 65% strain (p<0.05) among all three samples was observed. Samples using initial strains of 50, 75% were also prepared and tested, with results falling between those of the 25 and 100% initial strains.

Figure 3:
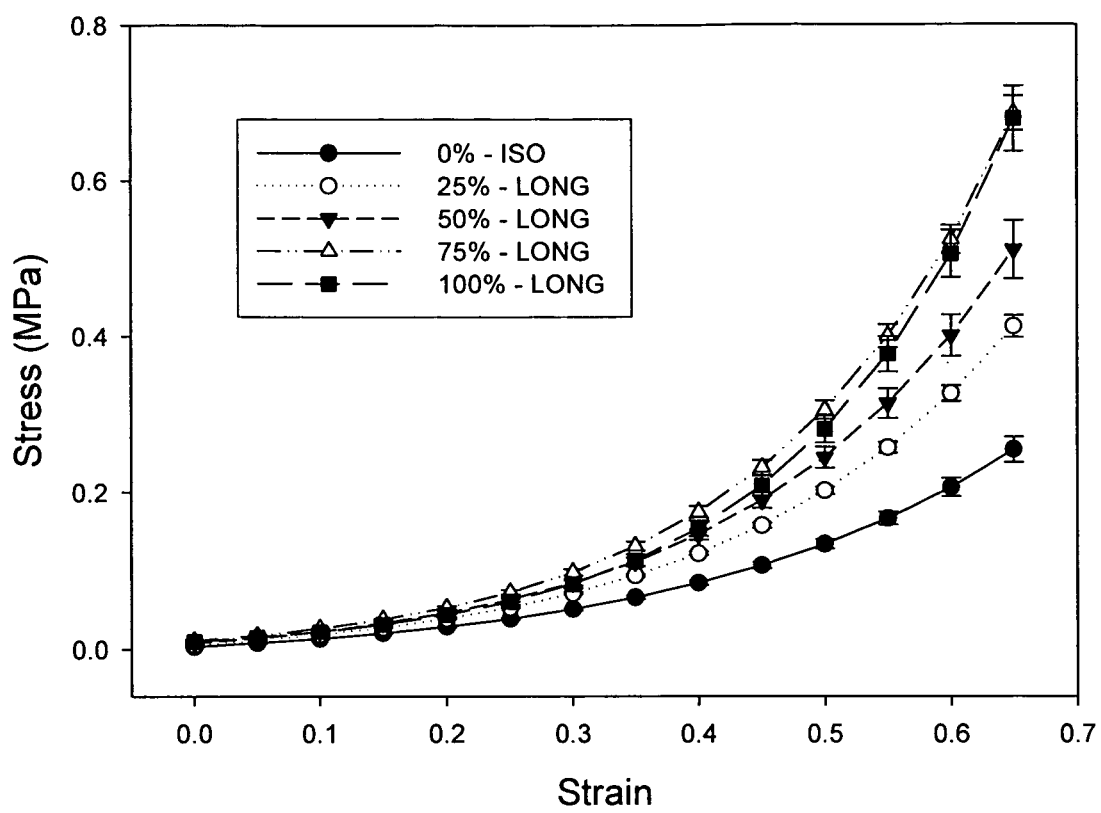
FIG. 3 shows the effect of initial strain (0, 25, 50, 75, and 100%) on the longitudinal stress-strain curves of anisotropic 10% PVA with 0.3% bacterial cellulose, following 6 thermal cycles.

FIGS. 1 and 2 show the effect of initial strain at a level of 25 and 100% on PVA-bacterial cellulose (6 cycles). Anisotropy is observed at the low initial strain of 25%. The difference between longitudinal and perpendicular directions increases with increasing initial strain. The increase is mainly due to the increase in stiffness in the longitudinal direction, although in the perpendicular direction, stiffness also decreases, but to a much lesser degree. FIG. 3 shows the results in the longitudinal direction as a function of initial strain, at increments of 25% between 0 and 100%. A gradual increase in strength in the longitudinal direction can be observed up to 75% initial strain, with no further increase to 100% strain. This results contrast that of PVA alone, where the increase in stiffness of the longitudinal direction was observed up to 100% initial strain.

Figure 4:
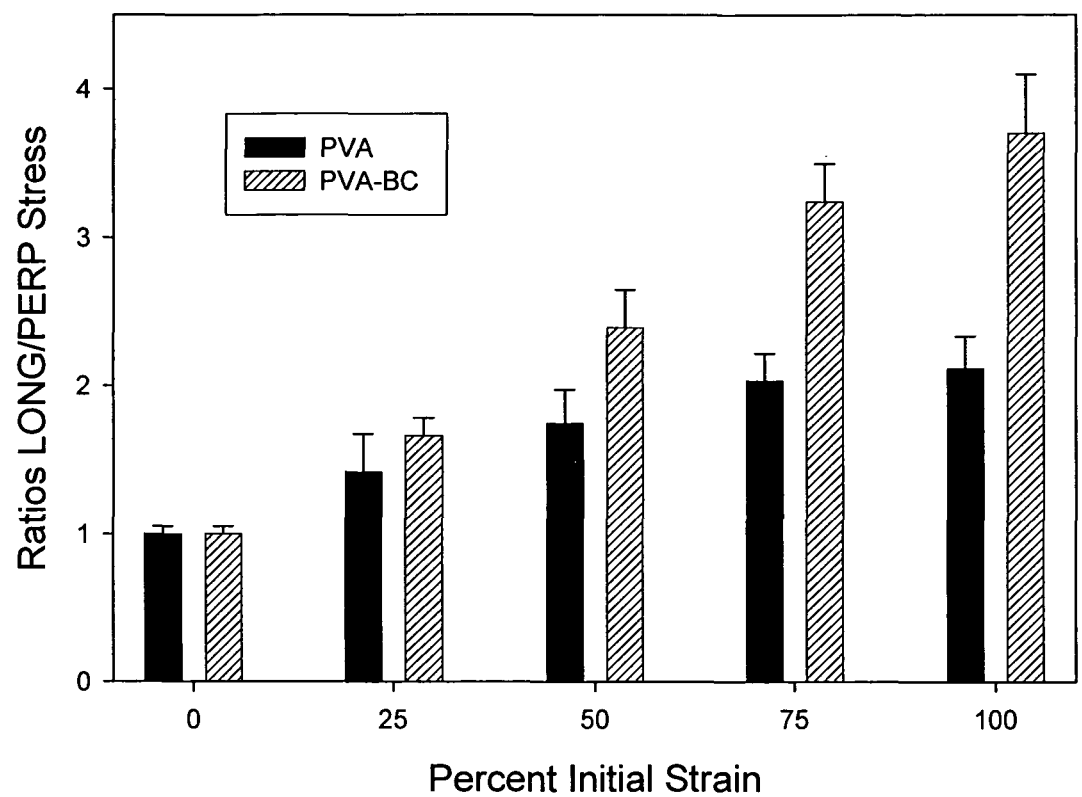
FIG. 4 shows a comparison of the effect of initial strain on the ratio of longitudinal to perpendicular stress at 65% strain (following 6 thermal cycles) between anisotropic 10% PVA and anisotropic 10% PVA with 0.3% bacterial cellulose nanocomposite.
Figure 5:
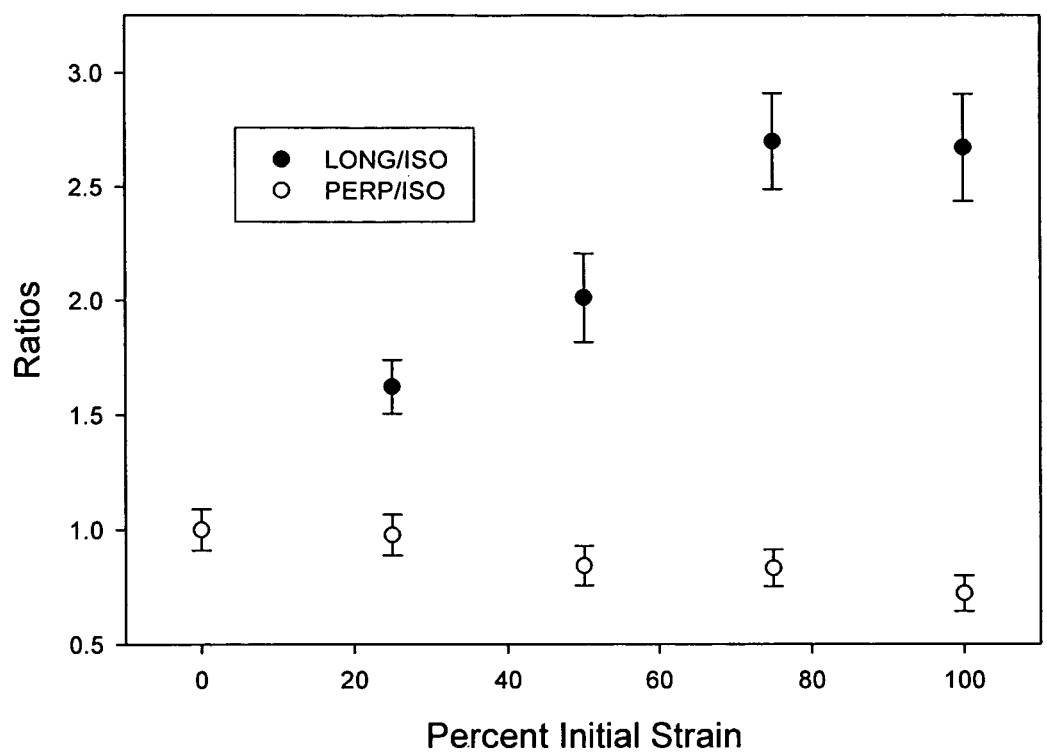
FIG. 5 plots the ratios of longitudinal to isotropic and perpendicular to isotropic stress (at 65% strain) as a function of initial strain (from 0 to 100%)

The degree of anisotropy can be more clearly quantified by calculating the ratio of stress of longitudinal to perpendicular directions as a function of initial strain at a strain of 65%, as seen in FIG. 4. The ratio increases monotonically from 1 (isotropic) to around 3.7 at an initial strain of 100%. The effect of initial strain on strength in the longitudinal and perpendicular directions (shown as ratios) is shown in FIG. 5. It can be seen that up to 75%, the initial strain has a much larger effect in the longitudinal direction. Hence, the overall mechanical properties are dominated by changes in the longitudinal direction leading to the observed leveling off of the longitudinal to perpendicular ratio at strains higher than 75% initial strain (statistically the same at 100% initial strain).

For PVA alone, the ratio leveled off at around 2 after reaching 75% initial strain. Therefore, the addition of a small amount of bacterial cellulose provided the unexpected result of almost doubling the anisotropic effect relative to that of anisotropic PVA alone.

FIG. 3 shows the stress-strain curves for the longitudinal samples as a function of initial strain. There is a clear trend of increase in stiffness in the longitudinal direction as the initial strain is increased from 0 to 75%, with the 100% samples being statistically the same as the 75%. The initial strain has a larger effect on the longitudinal direction than on the perpendicular direction. Results in the perpendicular direction (not shown) fell somewhat below the isotropic samples, except the samples initially strained to 25% which were found to be statistically the same as the isotropic control at 65% strain. In the longitudinal direction, a statistically significant difference of stress at 65% strain ($p<0.05$) was observed among all samples except the 75 and the 100% initial strain.

An alternate way to quantifying anisotropy is to calculate the ratio of stress in the longitudinal and perpendicular directions as a function of initial strain. FIG. 4 compares the effect of initial strain on the ratio of longitudinal to perpendicular stress at 65% strain (Cycle 6) between anisotropic 10% PVA and anisotropic 10% PVA with 0.3% bacterial cellulose, with 0% representing the isotropic controls. It can be seen that the stress ratio of the PVA-bacterial cellulose nanocomposite increases monotonically from 1 (0% isotropic control) to around 3.7±0.4 at 100% initial strain. This is a significant increase from the anisotropic PVA results, where the ratio of longitudinal to perpendicular stress increases to up to 2.1±0.2 at an initial strain of 75% and leveled off thereafter. When ANOVA was applied to the stress ratios of the PVA-bacterial cellulose samples, all samples were found to be statistically different, except the ratios at 75 and 100% initial strains ($p<0.05$).

The trend of the ratio of longitudinal to perpendicular stress can be better understood by examining the changes in stress in both the longitudinal and perpendicular directions as a function of initial strain. The ratios of longitudinal to isotropic and perpendicular to isotropic stress (at 65% strain) as a function of initial strain (from 0 to 100%) are shown in FIG. 5. It can be seen that increasing the initial strain has a much larger effect in the longitudinal direction for initial strains up to 75%. Initial strains larger than 100% were not investigated since straining marks on the surface of the hydrogel were noted for samples of PVA alone, as described elsewhere.

Example 4

Effect of Number of Thermal Cycles

Figure 6:
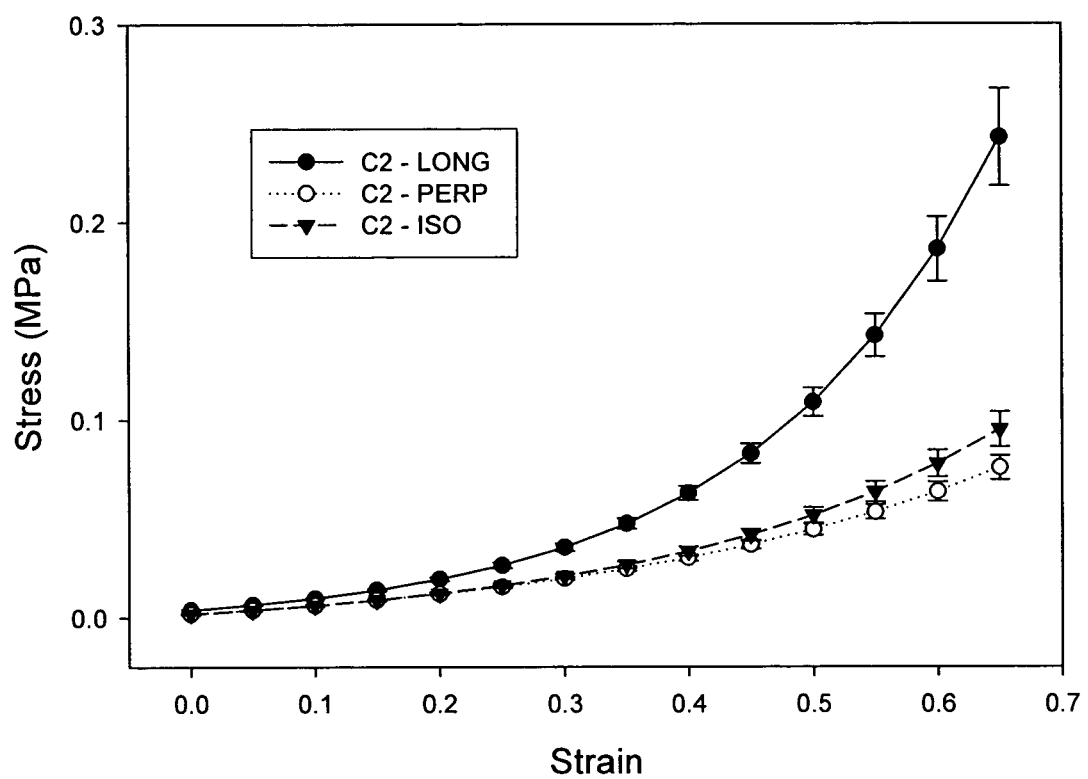
FIG. 6 shows the effect of 75% initial strain anisotropic 10% PVA with 0.3% bacterial cellulose, following 2 thermal cycles.
Figure 7:
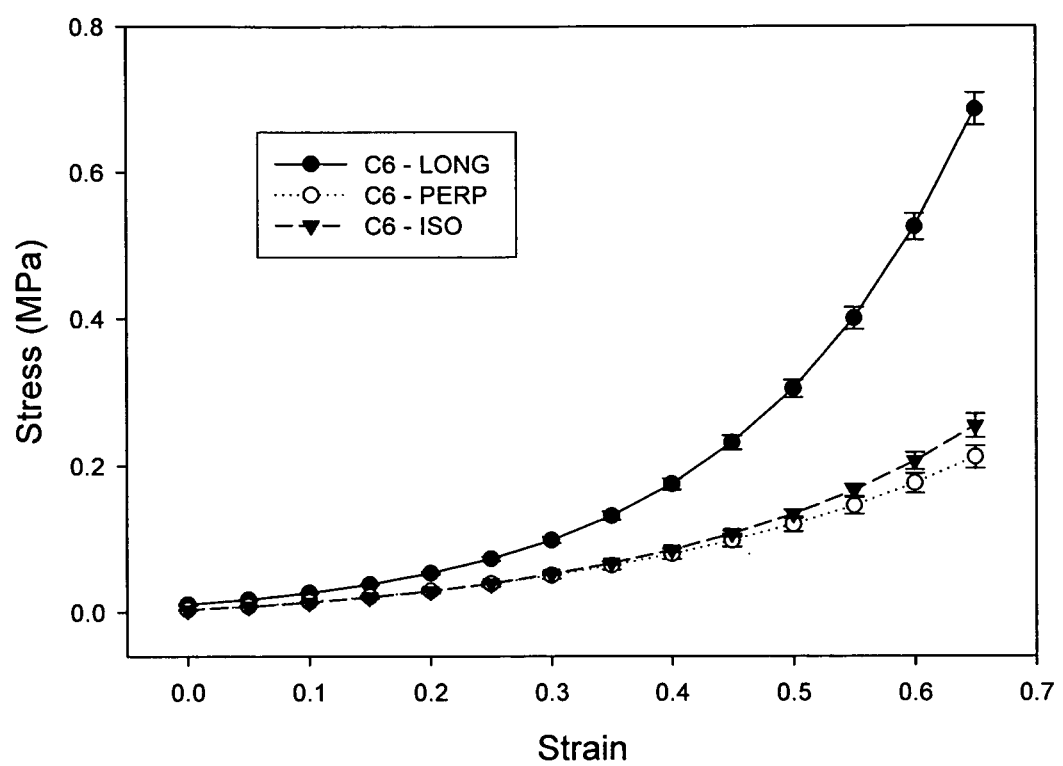
FIG. 7 shows the effect of 75% initial strain anisotropic 10% PVA with 0.3% bacterial cellulose, following 6 thermal cycles.

FIGS. 6 and 7 show the effect of 75% initial strain on 10% PVA with 0.3% bacterial cellulose at cycles 2 and 6, respectively, together with the isotropic control for the same cycle. Anisotropy was seen for all cycles, including cycle 4 (not shown). As seen before, data for the perpendicular samples falls lower than that for the isotropic control. In both FIGS. 6 and 7, a statistically significant difference of stress at 65% strain ($p<0.05$) was observed among all three samples.

Figure 8:
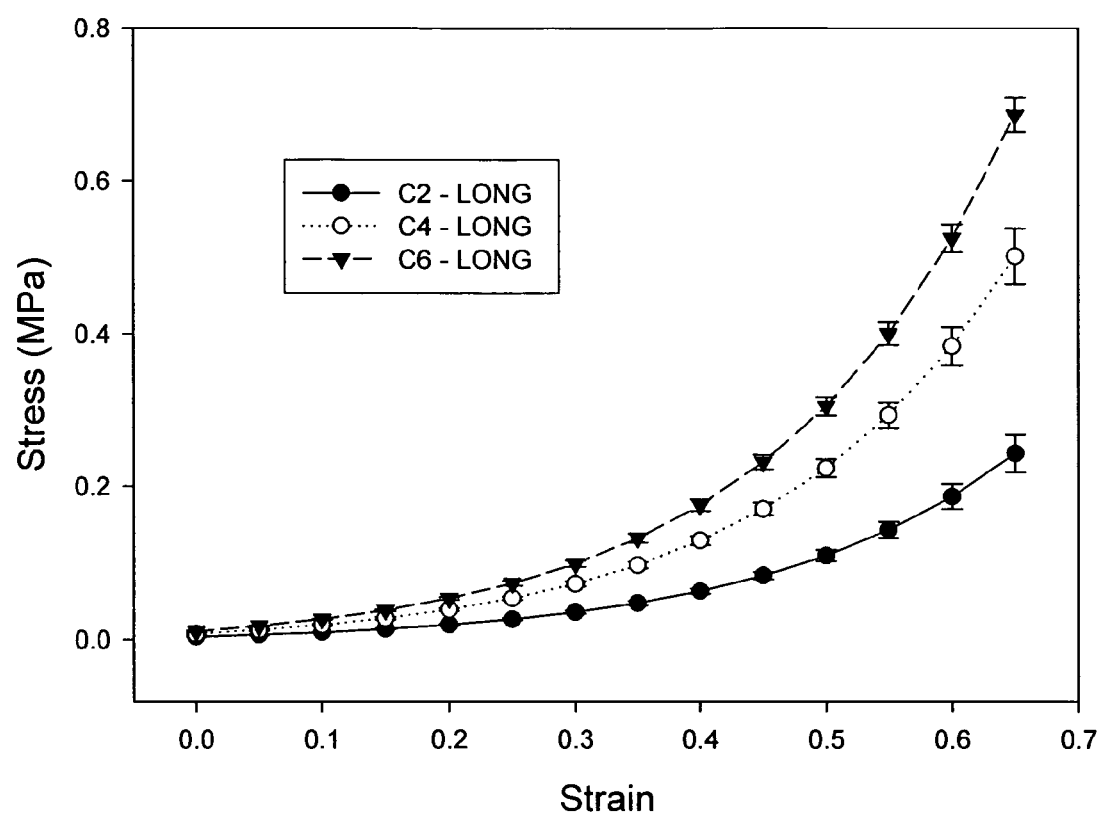
FIG. 8 shows the effect of number of thermal cycles (2, 4, and 6) on the longitudinal stress-strain curves of anisotropic 10% PVA with 0.3% bacterial cellulose (75% initial strain)

FIG. 8 compares the stress-strain curves of longitudinal samples as a function of number of thermal cycles (2, 4, and 6). The stress-strain curves of the perpendicular and isotropic samples were removed for clarity. The increase in stiffness with the number of cycles is clearly seen. A statistically significant difference of stress at 65% strain ($p<0.05$) was observed among all three samples.

Figure 9:
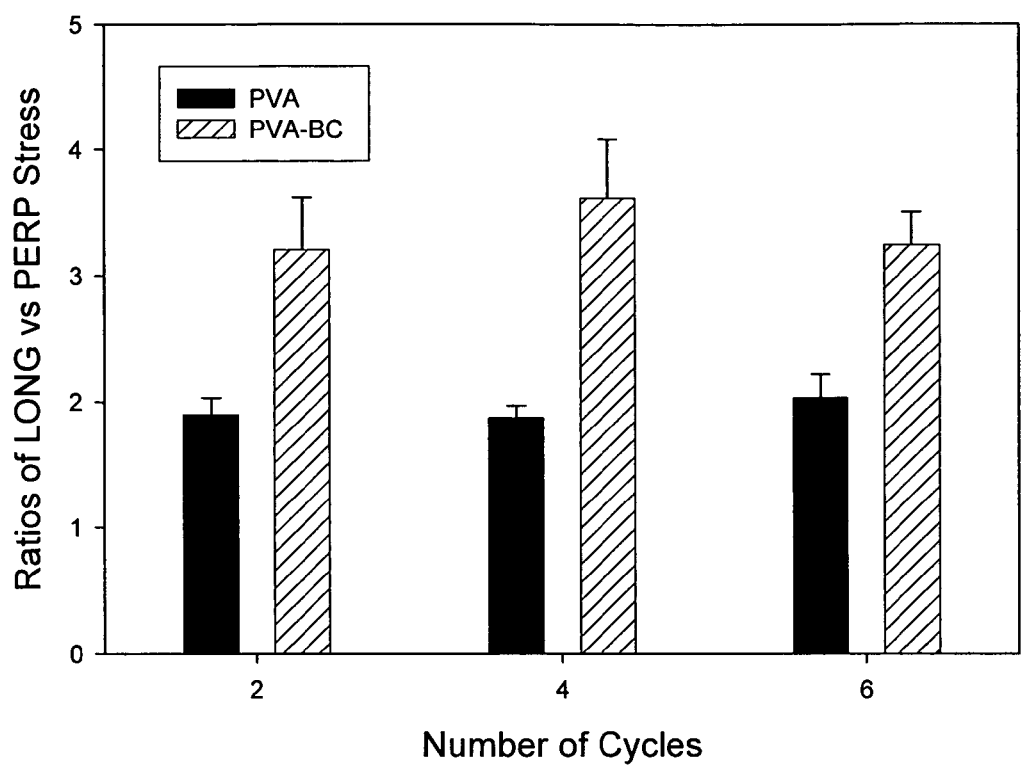
FIG. 9 shows a comparison of the effect of number of thermal cycles on the ratio of longitudinal to perpendicular stress at 65% strain (75% initial strain) between anisotropic 10% PVA and anisotropic 10% PVA with 0.3% bacterial cellulose nanocomposite.

Following the analysis approach used in a previous study, FIG. 9 compares the effect of number of thermal cycles on the ratio of longitudinal to perpendicular stress at 65% strain (75% initial strain) between anisotropic 10% PVA and anisotropic 10% PVA containing 0.3% bacterial cellulose. It is seen that the ratio of longitudinal to perpendicular stress for the PVA-bacterial cellulose nanocomposite is constant (3.3) regardless of number of cycles. Thus, the stiffness in both directions increases proportionally as the number of thermal cycles increases. As clearly seen, the anisotropic PVA ratio showed a similar trend, with a ratio of about 1.9 under similar conditions. When ANOVA was applied to the ratio for PVA-bacterial cellulose, all groups were found to be statistically the same ($p>0.05$). However, for each number of thermal cycle, the ratio for PVA and PVA-bacterial cellulose were found statistically different ($p<0.05$).

Example 5

Relationship to Porcine Aorta

Figure 10:
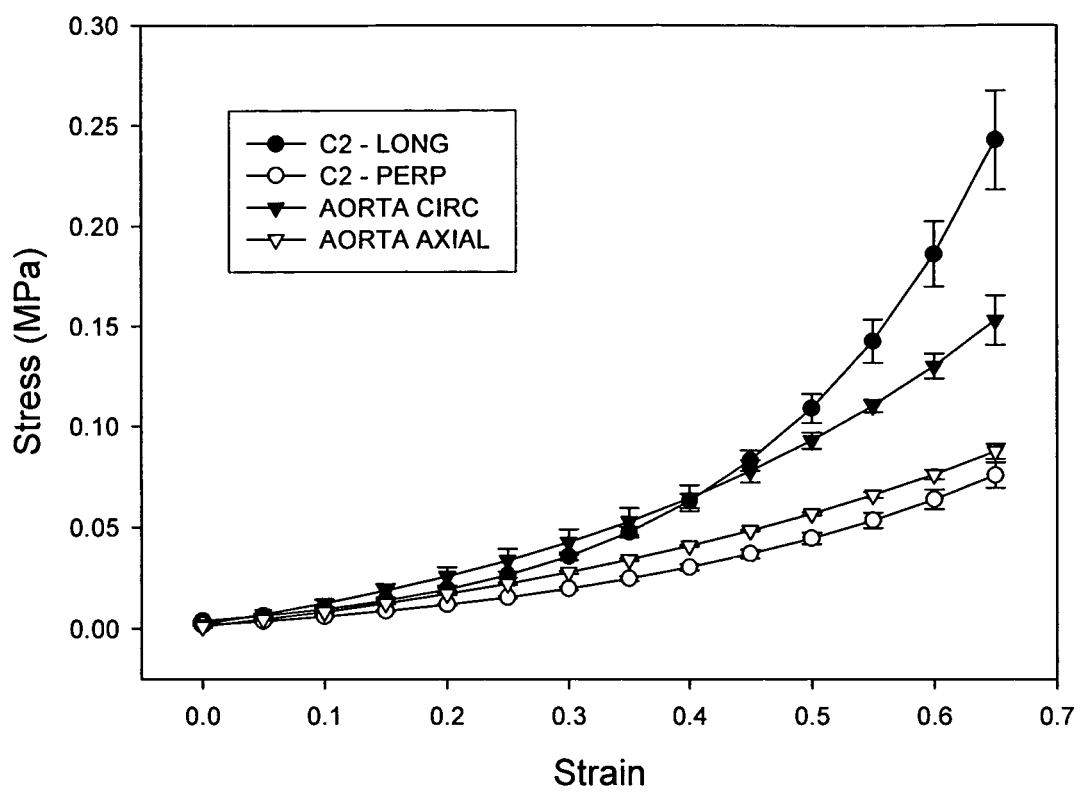
FIG. 10 reveals a close match within physiological range of the stress-strain curves of aorta (both directions) and anisotropic 10% PVA with 0.3% bacterial cellulose (75% initial strain and following 2 thermal cycles)

The mechanical response of porcine aorta in both circumferential and axial directions was compared with the anisotropic PVA-bacterial cellulose samples in order to assess a possible match of the mechanical properties for tissue replacement applications. The stress-strain curves for porcine aorta in both circumferential and axial directions had been previously shown to be similar to a 75% initial strain anisotropic PVA (cycle 3). As seen in FIG. 10, both the circumferential and axial curves are closely matched, within physiological range, by the anisotropic PVA-bacterial cellulose sample (75% initial strain and cycle 2). It is seen that this hydrogel displays the same tensile behavior as the aorta in both directions up to 45% strain. At higher strains, stiffness in the longitudinal direction increases to beyond that of the porcine aorta. ANOVA was applied to the stress at the average strain of 30% between systolic and diastolic cycles. The circumferential direction of aorta and the longitudinal direction of the PVA-bacterial cellulose samples showed no statistical difference. Similar statistical significance was also observed in the axial direction of aorta and the longitudinal direction of the PVA-bacterial cellulose samples.

To illustrate the use of this new anisotropic nanocomposite material in soft tissue replacement applications, the properties of porcine aorta were compared to the anisotropic PVA-bacterial cellulose nanocomposite. Aortic tissue is anisotropic, with a ratio of circumferential to axial stress of around 1.54 at a physiological strain of 30%. FIG. 10 shows that the tensile properties of porcine aorta within physiological range of 20-40% strain were closely matched in both directions by the 10% PVA containing 0.3% bacterial cellulose (cycle 2) processed at an initial strain of 75%.

Notably, the increase in stiffness at strains higher than 45% in the longitudinal direction is an improvement, since at larger than normal strains, as in the case of aneurisms and hypertension, the anisotropic conduit would have larger resistance to be further stretched. The anisotropic PVA-bacterial cellulose nanocomposite, along with the previously reported anisotropic PVA hydrogel are the only synthetic materials known to the inventors to be able to closely match the anisotropic response and mechanical properties displayed by porcine aorta within the physiological range.

Example 6

Stress Relaxation

The time-dependent relaxation response of the aortic tissue and that of 10% PVA with 0.3% bacterial cellulose (75% initial strain-cycle 2) were compared to assess the ability of the hydrogel to relax under tension as compared to the relaxation response of the tissue it might replace. The stress relaxation behavior was fitted using Eq. 2.

Figure 11:
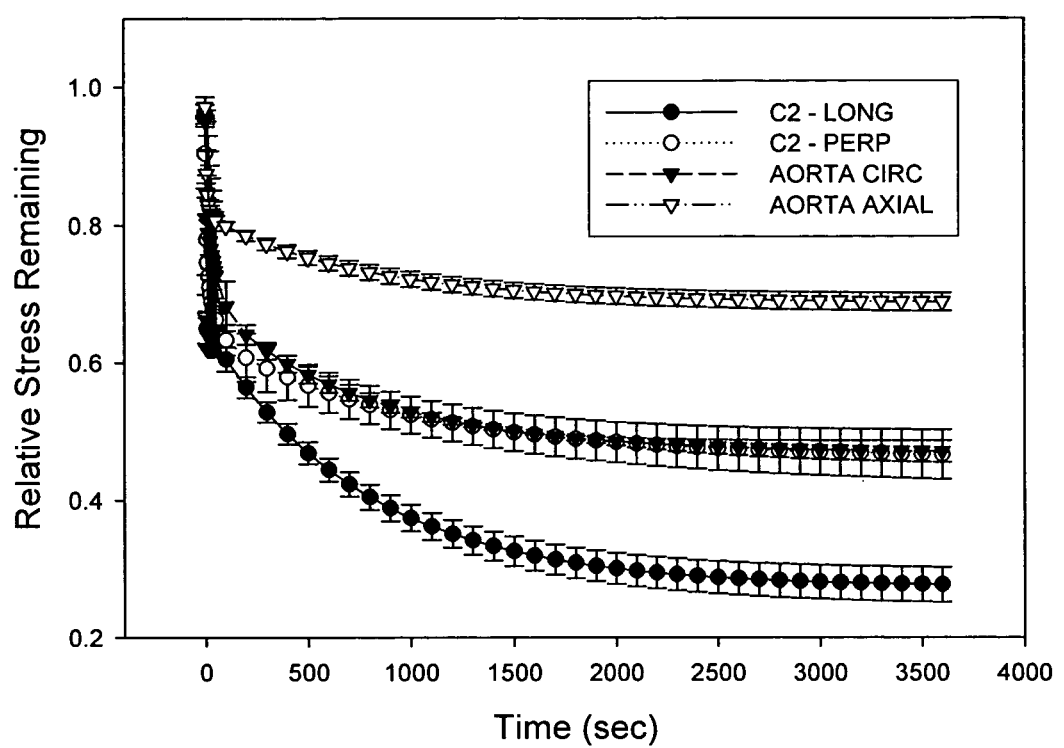
FIG. 11 shows the stress relaxation response for circumferential and axial directions of aorta and the anisotropic 10% PVA with 0.3% bacterial cellulose (75% initial strain, following 2 thermal cycles)

FIG. 11 shows the stress relaxation response for the 10% PVA with 0.3% bacterial cellulose (75% initial strain-cycle 2) and circumferential and axial directions of aorta. It is seen that the anisotropic PVA-bacterial cellulose nanocomposite relaxes to either the same or lower residual stress than aorta and at a similar rate to aortic tissue. It is interesting to note that both the circumferential samples of aorta and the longitudinal samples of the PVA-bacterial cellulose displayed a lower residual stress than the axial samples of aorta and the perpendicular samples of the PVA-bacterial cellulose samples, respectively. The fact that the PVA-bacterial cellulose nanocomposite relaxes as fast as and to either the same or lower relaxed stress than the aortic tissue indicate the ability of these PVA-bacterial cellulose nanocomposites to recover as fast as the native tissue in a cardiac cycle.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims. All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES

1. Kassab G S, Navia J A. Biomechanical considerations in the design of graft: the homeostasis hypothesis. Annu. Rev. Biomed. Eng. 2006; 8: 499-535.
2. Moustapha A, Anderson H V. Revascularization interventions for ischemic heart disease. Curr Opin Cardiol 2000; 15: 463-471.
3. Popma J J, Sawyer M, Selwyn A P, Kinlay S. Lipid-lowering therapy after coronary revascularization. Am J Cardiol 2000; 86: 18H-28H.
4. Haruguchi H, Teraoka S., Intimal hyperplasia and hemodynamic factors in arterial bypass and arteriovenous grafts: A review. J Artif Organs 2003; 6: 227-235.
5. Thomas A C, Campbell G R, Campbell J H. Advances in vascular tissue engineering. Cardiovasc Pathol 2003; 12: 271-276.
6. Schoen F J, Levy R J. Founder's Award, 25th Annual Meeting of the Society for Biomaterials, perspectives. Providence, R.I., Apr. 28-May 2, 1999. Tissue heart valves: current challenges and future research perspectives. Journal of biomedical materials research 1999; 47(4):439-65.
7. Fung Y C. Biomechanics: Mechanical Properties of Living Tissues. New York: Springer-Verlag; 1993. 568 p.
8. Hayash K, Stergiopulos N, Meister J, Greenwald S E, Rachev A. Techniques in the determination of the mechanical properties and constitutive laws of arterial walls. Boca Raton, Fla.: CRC Press; 2001.
9. Abe H, Hayashi K, Sato M, editors. Data book on mechanical properties of living cells, tissues, and organs. Tokyo: Springer-Verlag; 1996.
10. Xue L, Greisler Howard P. Biomaterials in the development and future of vascular grafts. Journal of vascular surgery 2003; 37(2):472-80.
11. Fussell G, Thomas J, Scanlon J, Lowman A, Marcolongo M. The effect of protein-free versus protein-containing medium on the mechanical properties and uptake of ions of poly(vinyl alcohol)/poly(vinyl pyrrolidone) hydrogels. Journal of Biomaterials Science, Polymer Edition 2005; 16(4):489-503.
12. Chowdhury M N K, Alam A K M M, Dafader N C, Haque M E, Akhtar F, Ahmed M U, Rashid H, Begum R. Radiation processed hydrogel of poly (vinyl alcohol) with biodegradable polysaccharides. Bio-Medical Materials and Engineering 2006; 16(3):223-228.
13. Hoffman, A. S. "Hydrogels for Biomedical Applications." Advanced Drug Delivery Reviews 54.1 (2002): 3-12.
14. Park, H. N., and K. Park. "Hydrogels in Bioapplications." Hydrogels and Biodegradable Polymers for Bioapplications. Eds. R. M. Ottenbrite, S. J. Huang, and Kinam Park. Washington, D.C.: ACS Symposium Series 627, 1994. 2-10.
15. Rosiak, J. M., and F. Yoshii. "Hydrogels and Their Mechanical Applications." Nuclear Instruments and Methods in Physics Research B 151.1-4 (1999): 56-64.
16. Ratner, B. D., et al., eds. Biomaterials Science: An Introduction to Materials in Medicine. San Diego: Academic Press, 1996.
17. Yannas, I. V., E. Lee, D. P. Orgill, "Synthesis and Characterization of a Model Extracellular Matrix that Induces Partial Regeneration of Adult Mammalian Skin." Proc. Natl. Acad. Sci. 86 (1989): 933-7.
18. Migliaresi, C., L. Nicodemo, and L. Nicolais. "Hydrogels for Artificial Tendons." Hydrogels in Medicine and Pharmacy. Ed. N. A. Peppas. Vol. 3. Boca Raton, Fla.: CRC Press, 1987.83-94.
19. Gordon, M. J. "Controlling the Mechanical Properties of PVA Hydrogels For Biomedical Applications." Diss. Western Ontario U., 1999.
20. Hui, A. J. "Hydrogel-Based Artificial Heart Valve Stent Material." Diss. Western Ontario U., 1998.
21. Sefton, M. V. "Heparinized Hydrogels." Hydrogels in Medicine and Pharmacy. Ed. N. A. Peppas. Vol. 3. Boca Raton, Fla.: CRC Press, 1987. 17-52.
22. Korsmeyer, R. W., et al. "Mechanisms of Potassium Chloride Release from Compressed, Hydrophilic, Polymeric Matrices; Effect of Entrapped Air" Journal of Pharmaceutical Science 72 (1983): 1189-91.
23. Vyavahare, N. R., et al. "Current Progress in Anticalcification for Bioprosthetic and Polymeric Heart Valves." Cardiovascular Pathology 6.4 (1997): 219-229.
24. Peppas, N. A. "Other Biomedical Applications of Hydrogels." Hydrogels in Medicine and Pharmacy. Ed. N. A. Peppas. Vol. 3. Boca Raton, Fla.: CRC Press, 1987.177-86.
25. Hassan, C. M., and N. A. Peppas. "Structure and Applications of Poly(vinyl alcohol) Hydrogels Produced by Conventional Crosslinking or by Freezing/Thawing Methods." Advances in Polymer Science 153 (2000): 37-65.
26. Lozinsky, V. I., and F. M. Plieva. "Poly(vinyl alcohol) Cryogels Employed as Matrices for Cell Immobilization. 3. Overview of Recent Research and Developments." Enzyme and Microbial Technology 23.3-4 (1998): 227-42.
27. Peppas, N. A., and C. M. Hassan. "Structure and Applications of PVA Hydrogels Produced by Freezing/Thawing Methods." Advances in Polymer Science 8 (2000): 37-41.
28. Cascone, M. G., et al. "Evaluation of Poly(vinyl alcohol) Hydrogels as a Component of Hybrid Artificial Tissues." Journal of Materials in Science: Materials in Medicine 6 (1995): 71-5.
29. Ku, D. N., L. G. Braddon, and D. M. Wootton. Poly(vinyl alcohol) Cryogel U.S. Pat. No. 5,981,826 (1999).
30. Mori, Y., H. Tokura, and M. Yoshikawa. "Properties of Hydrogels Synthesized by Freezing and Thawing Aqueous 30. Polyvinyl Alcohol Solutions and their Applications." Journal of Materials Science 32 (1997): 491-6.
31. Stauffer, S. R., and N. A. Peppas. "Poly(vinyl alcohol) Hydrogels Prepared by Freezing-Thawing Cyclic Processing." Polymer 33.18 (1992): 3932-5.
32. Chu, K. C., and B. K. Rutt. "Polyvinyl Alcohol Cryogel: An Ideal Phantom Material for MR Studies of Arterial Flow and Elasticity." Magnetic Resonance in Medicine 37 (1997): 314-9.
33. Wan, W. K., et al. "Anisotropic Polyvinyl Alcohol Hydrogel for Cardiovascular Applications." Journal of Biomedical Materials Research (Applied Biomaterials) 79 (2006): 305-311.
34. Eichhorn, S. J., et al. "Review Current International Research into Cellulosic Fibres and Composites." Journal of Materials Science 36.9 (2001): 2107-31.
35. Joseph, G. A. "Studies of Bacterial Cellulose Production in Agitated Culture." Diss. Western Ontario U., 2001.
36. Klemm, D., et al. "Bacterial Synthesized Cellulose—Artificial Blood Vessel for Microsurgery." Progress in Polymer Science 26.9 (2001): 1561-603.
37. Uryu, M., and K. Tokura. Composite Polymer Materials and Process for Producing the Same U.S. Pat. No. 6,274,652 (2001).
38. Wan, W. K., et al. "The Polyvinyl Alcohol—Bacterial Cellulose System as a New Nanocomposite for Biomedical Applications." Journal of Biomedical Materials Research (Applied Biomaterials) 79 (2006): 245-253.
39. Wan, W. K., et al. "Anisotropic Polyvinyl Alcohol—Bacterial Cellulose Nanocomposite for Biomedical Applications." Journal of Biomedical Materials Research (Applied Biomaterials) 86 (2008): 444-452.
40. Wan W K, Campbell G, Zhang Z F, Hui A J, Boughner D R. Optimizing the tensile properties of polyvinyl alcohol hydrogel for the construction of a bioprosthetic heart valve stent. J Biomed Mater Res 2002; 63: 854-861.
41. Lee J M, Haberer S A, Boughner D R. The bovine pericardial xenograft. I. Effect of fixation in aldehydes without constraint on the tensile viscoelastic properties of bovine pericardium. J Biomed Mater Res 1989; 23: 457-475.
42. Guhados G, Wan W, Hutter J L. Measurement of the elastic modulus of single bacterial cellulose fibers using atomic force microscopy. Langmuir 2005; 21:6642-6646.
42. Millon L E, Nieh M-P, Hutter J L, Wan W-K. SANS characterization of an anisotropic polyvinyl alcohol hydrogel with vascular applications. Macromolecules 2007; 40:3655-3662.
44. Ricciardi R, Auriemma F, De Rosa C, Laupretre F. X-ray diffraction analysis of poly(vinyl alcohol) hydrogels obtained by freezing and thawing techniques. Macromolecules 2004; 37: 1921-1927.
45. Ricciardi R, D'Errico G, Auriemma F, Ducouret G, Tedeschi A M, De Rosa C, Laupretre F, Lafuma F. Short time dynamics of solvent molecules and supramolecular organization of poly (vinyl alcohol) hydrogels obtained by freeze/thaw techniques. Macromolecules 2005; 38:6629-6639.
46. Ricciardi R, Mangiapia G, Lo Celso F, Paduano L, Triolo R, Auriemma F, De Rosa C, Laupretre F. Structural organization of poly(vinyl alcohol) hydrogels obtained by freezing and thawing techniques: A SANS study. Chem Mater 2005; 17: 1183-1189.
47. Willcox P J, Howie D W Jr., Schmidt-Rohr K, Hoagland D A, Gido S P, Pudjijanto S, Kleiner L W, Venkatraman S. Microstructure of poly(vinyl alcohol) hydrogels produced by freeze/thaw cycling. J Polym Sci B: Polym Phys 1999; 37:3438-3454.
48. Baeckdahl H, Helenius G, Bodin A, Nannmark U, Johansson B R, Risberg B, Gatenholm P. Mechanical properties of bacterial cellulose and interactions with smooth muscle cells. Biomaterials 2006; 27:2141-2149.
49. Helenius G, Baeckdahl H, Bodin A, Nannmark U, Gatenholm P, Risberg B. In vivo biocompatibility of bacterial cellulose. J Biomed Mater Res A 2006; 76:431-438.
50. Astley O M, Chanliaud E, Donald A M, Gidley M J. Tensile deformation of bacterial cellulose composites. Int J Biol Macromol 2003; 32:28-35.
51. Gindl W, Keckes J. Tensile properties of cellulose acetate butyrate composites reinforced with bacterial cellulose. Compos Sci Technol 2004; 64:2407-2413
52. Chen et al. J. Vascular Surgery, 1995, 22, 237-247.

Therefore what is claimed is:

1. A process of producing a nanocomposite hydrogel with an anisotropic stress-strain curve, comprising the steps of:
    forming a suspension of microbially-produced cellulose fibers in a solvent wherein said cellulose comprises fibers having nanometer scale cross sectional dimensions, the cellulose fibers having been formed via agitated culture or shaken culture, thereby preventing the formation of a pellicle;
    adding a hydrogel-forming material to the cellulose suspension, such that the hydrogel-forming material is dissolved in the suspension;
    crosslinking said hydrogel-forming material to obtain a nanocomposite hydrogel;
    applying a longitudinal strain to said nanocomposite hydrogel; and
    thermal cycling said nanocomposite hydrogel over a predetermined temperature range at least once while maintaining said longitudinal strain;
    such that said nanocomposite hydrogel has an increased ratio of longitudinal to perpendicular stress under application of strain, compared to an anisotropic hydrogel formed in the absence of said cellulose;
    wherein the hydrogel-forming material is present in an amount from 5% by weight to 15% by weight and the microbially-produced cellulose fibers are present in a range from 0.05% by weight to 0.5% by weight;
    wherein the hydrogel-forming material is selected from the group consisting of polyvinyl alcohol (PVA), poly(vinyl pyrrolidone) (PVP), poly(ethylene glycol) (PEG), poly (hydroxyethyl methacrylate) (PHEMA) and polyacrylamide; and
    wherein the solvent is a hydroxylic solvent or an aprotic solvent capable of forming effective hydrogen bonding to dissolve the hydrogel material.

2. The process according to claim 1 wherein said crosslinking of said hydrogel-forming material includes physical crosslinking.

3. The process according to claim 2 wherein said physical crosslinking includes low temperature thermal cycling.

4. The process according to claim 1 wherein said solvent is distilled water.

5. The process according to claim 1 where said longitudinal strain strains said nanocomposite hydrogel over a range including 25% to 100% of an unstrained length of said nanocomposite hydrogel.

6. The process according to claim 5 where said longitudinal strain strains said nanocomposite hydrogel to a strain of 75% of an unstrained length of nanocomposite hydrogel.

7. The process according to claim 1 wherein said solvent is prepared by heating at a temperature of about 80° C. to about 100° C. for about 2 to 4 hours.

8. The process according to claim 1 wherein said step of thermal cycling said nanocomposite hydrogel over a predetermined temperature range at least once involves freezing and thawing said nanocomposite hydrogel, maintaining said hydrogel in a frozen state for a predetermined holding period, and thawing said nanocomposite hydrogel.

9. The process according to claim 1 wherein thermal cycling said nanocomposite hydrogel over a predetermined temperature range is performed a number of times ranging from 1 to 6.

10. The process according to claim 9 wherein the concentration of the hydrogel-forming material in said solvent is about 10%.

11. The process according to claim 1 wherein said cellulose of microbial origin is bacterial cellulose produced by the species *Acetobacter xylinum*.

12. The process according to claim 1, wherein said nanocomposite hydrogel is transferred into one or more molds of the shape of a final material, device or apparatus following said step of crosslinking said hydrogel-forming material.

13. The process according to claim 12 wherein the final material, device or apparatus is selected from replacement soft tissue, an ultrasound or radio frequency thermal therapy transmission pad, a substitute for an ice bag, a denture base, dental implants, soft contact lens material, wound covering bandage, neurological dressings, catheter covering dressing, dialysis membranes, coatings for cardiovascular stents, coatings for cranial stents, and membranes for tissue guided regeneration and phantoms for medical-related use.

14. The process according to claim 13, wherein the soft tissue is selected from vascular vessels, coronary arteries, heart valve leaflets, heart valve stent, cartilage, ligaments and skin.

15. The process according to claim 14, wherein the vascular vessels are selected from aorta and coronary arteries.

16. The process according to claim 1 wherein said concentration of cellulose in said solvent is about 0.3%.

17. The process according to claim 1 wherein said step of thermal cycling said nanocomposite hydrogel over a predetermined temperature range at least once involves cooling the nanocomposite hydrogel from a first temperature of about 15° C. to 30° C. to a second temperature of about −15° C. to −30° C., maintaining said second temperature for a holding time, and heating said nanocomposite hydrogel back to a temperature approximately equal to said first temperature.

18. The process according to claim 17 wherein said step of thermal cycling said nanocomposite hydrogel over a predetermined temperature range at least once involves cooling the nanocomposite hydrogel from a first temperature of about 20° C. to a second temperature of about −20° C., maintaining said second temperature for a holding time, and heating said nanocomposite hydrogel back to a temperature approximately equal to said first temperature.

19. The process according to claim 17 wherein the rate of change of temperature during thermal cycling is in the range of about 0.05° C. to 0.5° C. per minute.

20. The process according to claim 19 wherein the rate of change of temperature during thermal cycling is about 0.1° C. per minute.

21. The process according to claim 17 wherein said holding time is about 1 hour.

22. The process according to claim 1, further comprising incorporating one or more bioagents into said nanocomposite hydrogel.

23. The process according to claim 22, wherein said one or more bioagents are incorporated into said solvent prior to said step of crosslinking.

24. The process according to claim 22, wherein the one or more bioagents are selected from cells, antibodies, cytokines, thrombins, thrombin inhibitors, proteases, anticoagulants, heparin, growth factors, collagen crosslinking inhibitors, matrix inhibitors, glycosaminoglycans and antimicrobial agents.

25. The process according to claim 24, wherein the cells are eukaryotic cells.

26. The process according to claim 25, wherein the eukaryotic cells are vascular cells or connective tissue cells.

27. The process according to claim 26, wherein the vascular cells are endothelial cells, smooth muscle cells or fibroblasts.

28. The process according to claim 22, wherein the bioagent is heparin.

* * * * *